United States Patent [19]
Fan et al.

[11] Patent Number: 5,624,391
[45] Date of Patent: *Apr. 29, 1997

[54] ELASTIC BANDAGE

[76] Inventors: Lidi Fan, No. 18 Dong San Jia Li, Xiao Mu, Qiao Lu, Shanghai 200032; Dongfa Xu, 233/1 Xin Ma Lu, Pu Dong Zhou Pu, Shanghai 201318; Jinshu Cao; Jianming Lu, both of No. 180 Feng Lin Lu, Shanghai 200030, all of China

[*] Notice: The term of this patent shall not extend beyond the expiration date of Pat. No. 5,395,307.

[21] Appl. No.: 349,430

[22] Filed: Dec. 5, 1994

Related U.S. Application Data

[63] Continuation of Ser. No. 193,788, Feb. 8, 1994, Pat. No. 5,395,307.

[30] Foreign Application Priority Data

Feb. 9, 1993 [CN] China ................. 93203698.8

[51] Int. Cl.$^6$ ........................................ A61F 3/00
[52] U.S. Cl. ........................ 602/63; 602/75; 128/DIG. 15
[58] Field of Search ............. 602/1, 5, 12, 14, 602/19, 20, 32, 36, 41, 60, 63, 75, 78; 128/DIG. 15

[56] References Cited

U.S. PATENT DOCUMENTS

| | | | |
|---|---|---|---|
| 4,296,744 | 10/1981 | Palumbo | 602/63 X |
| 4,370,978 | 2/1983 | Palumbo | 602/63 X |
| 5,076,288 | 12/1991 | Millard et al. | 128/DIG. 15 X |
| 5,095,894 | 3/1992 | Marble | 128/DIG. 15 X |
| 5,214,874 | 6/1993 | Faulkner | 128/DIG. 15 X |
| 5,259,397 | 11/1993 | McCabe | 602/75 X |
| 5,267,952 | 12/1993 | Gardner | 602/63 X |

FOREIGN PATENT DOCUMENTS

91/06265  5/1991  WIPO ................... 602/20

Primary Examiner—Sam Rimell
Attorney, Agent, or Firm—Abelman, Frayne & Schwab

[57] ABSTRACT

The invention relates to an elastic bandage for medical use. A base part of the bandage is made of pure cotton cloth or other fabric with a cloth cover on a transverse side in which a drainage aperture is defined. On opposite transverse sides of the base part there are respectively provided two outlying parts of the bandage with a drainage aperture in each of them. On opposite transverse sides of the base part there are respectively two safety bands and two suspenders on a longitudinal side of base part. The safety bands and the outlying parts are fastened together with fasteners.

7 Claims, 1 Drawing Sheet

5,624,391

ELASTIC BANDAGE

This application is a continuation of Ser. No. 08/193,788 filed Feb. 8, 1994 now U.S. Pat. No. 5,395,307.

FIELD OF THE INVENTION

The present invention is an elastic bandage for medical use.

BACKGROUND OF THE INVENTION

Existing post-operative bandages, popularly known as "multi-head bandages", are made of pure cotton or unwoven fabric and comprise a piece of rectangular cloth with a number of cloth strips on two opposing sides of the cloth. A patient, after having an operation in the chest or abdomen, would have this bandage applied for protection and stabilization of the operation wound or incision. This type of bandage usually requires two medical personnel to wind it around the wounded portion of a patient. Once the bandage is wound around the patient, the cloth strips on opposite sides are successively overlapped on each other and tightly fastened together. If a drainage tube or other drainage device is needed for the wound, it may be placed in a gap between the cloth strips of the bandage.

The prior art devices suffer from the disadvantage of being cumbersome. The prior bandage requires two skilled individuals for application. A patient cannot handle the bandage himself. Additionally, the prior bandage is not elastic and applies uneven pressure to a wound. Uneven pressure on a wound may result in uneven healing of the wound and discomfort to the wearer.

The prior bandage is susceptible to loosening or displacement due to patient motion. If the bandage is wound too tightly, the patient may suffer a feeling of constriction. If the bandage is wound too loosely, the analgesic effect from the pressure of the bandage is lost. Also, because the drainage tube is placed between a gap in the cloth strips of the bandage, it is liable to be become twisted or constricted and its drainage capacity impeded.

SUMMARY OF THE INVENTION

The present invention discloses a bandage for medical use made of elastic and other fabric. It has the advantages of being elastic, providing even pressure to the wound, and providing an analgesic effect from the pressure without a feeling of constriction. Its elasticity prevents loosening or sliding due to patient motion. Its substantially even pressure and stability allows for the smooth and clean healing of a wound. For added durability, a preferred embodiment of the present invention discloses loops for removably securing receptacles such as bottles or bags on the bandage and drainage openings in the bandage to facilitate unimpeded drainage from a wound. Further improvement includes the addition of a relatively thin padding sheet, provided in the area where the various bandage members are connected.

STATEMENT OF THE INVENTION

The elastic bandage comprises a base bandage member, two outlying bandage members, a cloth cover, and corresponding fasteners. It may also comprise two relatively thin padding sheets, two safety bandage members, two suspenders, and corresponding connectors and fasteners.

In its preferred embodiment, he base bandage member is made of pure cotton or other fabric. As well, it is isosceles trapezoidal in shape if used as a chest bandage, to conform to the V-shape, larger on the upper part than on the lower part, of the typical human torso. It is rectangular in shape if used in other applications.

The two outlying bandage members are made of elastic materials. Each has a length substantially equal to that of the base bandage member, for purposes of providing evenly distributing pressure throughout the bandage. Each is either trapezoidal or rectangular in shape, corresponding to the shape of the base bandage member. Each is sewingly joined on a proximal edge, respectively with opposite transverse edges of the base bandage member. Each has fasteners located on a distal edge of each outlying bandage member, so that the two outlying bandage members may be fastened together at their distal ends. At least one outlying member also has a centrally located fastener, so that it may be connected to a corresponding safety bandage member.

The cloth cover is made of cotton or other sterile material. It is sewingly attached to the location where one of the outlying bandage members is joined with the base bandage member. The cloth cover and at least one the outlying bandage members contain corresponding drainage openings. A tube may be inserted in the drainage opening to facilitate draining of the wound.

Further, the bandage may contain a two relatively thin padding sheets. This provides added durability. The padding sheets are made of foamed plastic or other cushioning materials. They have width substantially equal to that of the outlying and base bandage members. The sheets are provided around the two joints formed where each outlying bandage member is connected to the base bandage member. Also, at least one of the joints may contain a loop for removably securing receptacles such as bottles or bags on the bandage. Such a receptacle may be connected to a tube inserted in the drainage openings, so that drainage from the wound may be received and contained.

Two safety bandage members may be used in the invention to increase pressure upon the wound, further preventing unwanted motion of the bandage. The safety bandage members are made of elastic fabric. Each is trapezoidal or rectangular in shape, corresponding to the shape of the base bandage member. Each is sewingly attached on a proximal edge respectively to opposite locations where the outlying bandage members are joined with the base bandage member, on a side of the base bandage member opposite the cover cloth. The length of the safety bandage members is less than that of the base and outlying bandage members, to provide pressure beyond that available from the base and outlying bandage members alone. Fasteners are located on a distal edge of each safety bandage member and on a central part of at least one safety bandage member, so that at least one safety bandage member may be fastened to at least one, corresponding outlying member, and so that the two safety bandage members may be fastened together at their distal ends.

Two suspenders may be used to help support the bandage upon the wound, in applications such as a chest bandage. The suspenders are made of elastic fabric. Each suspender is sewingly attached to a longitudinal edge of the base bandage member and is spaced apart from the other. Two connectors are each located on a longitudinal edge of each outlying bandage member, corresponding to the edge where the suspenders are located. The suspenders may be connected to the connectors. The bandage is operated as follows:

The base bandage member is placed on a side of a body opposite the wound to be bandaged. The cloth cover is brought around the body to cover the wound. Each outlying bandage member is brought around its respective side of the body and is fastened to the other.

Additionally, each safety bandage member is brought around its respective side of the body. At least one safety member is fastened to at least one outlying bandage member. Then the two safety bandage members are fastened together.

Further, each suspender is pulled up over the top of the body portion being bandaged. Each suspender is then pulled down and respectively connected to a corresponding connector.

BRIEF DESCRIPTION OF THE DRAWINGS

FIG. 3 is a sectional view of the preferred embodiment as it appears when fastened for use.

DESCRIPTION OF THE PREFERRED EMBODIMENT

Figure 1:
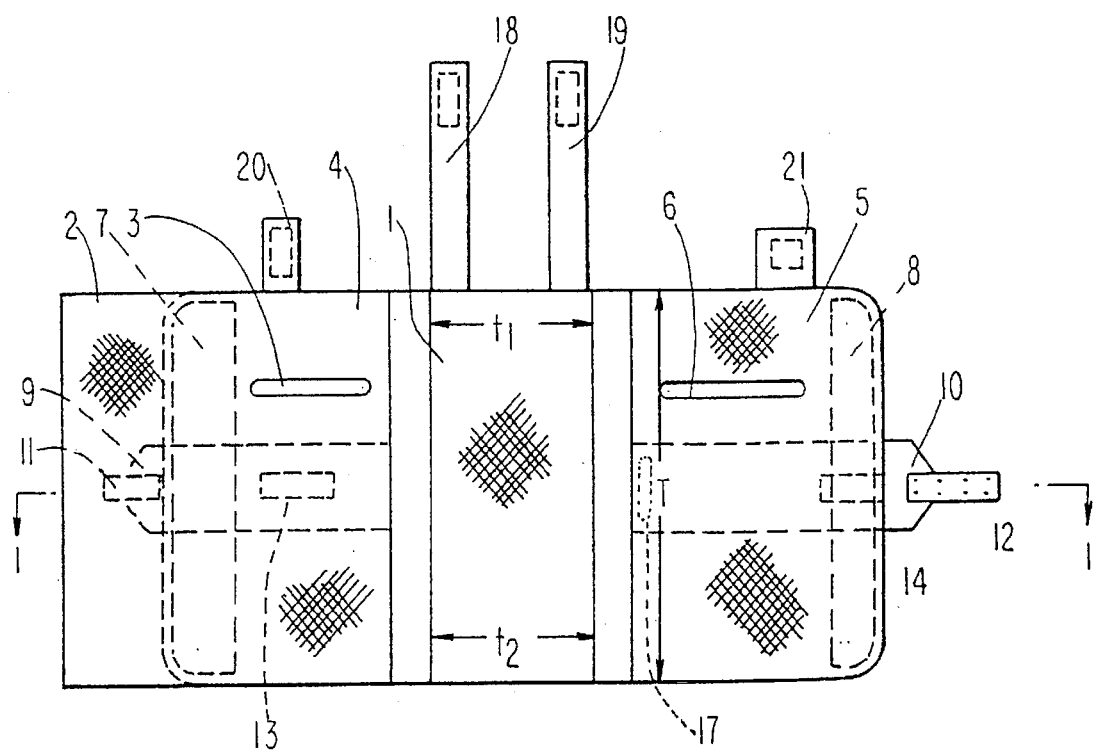
FIG. 1 is a front view of a preferred embodiment of the invention.
Figure 2:
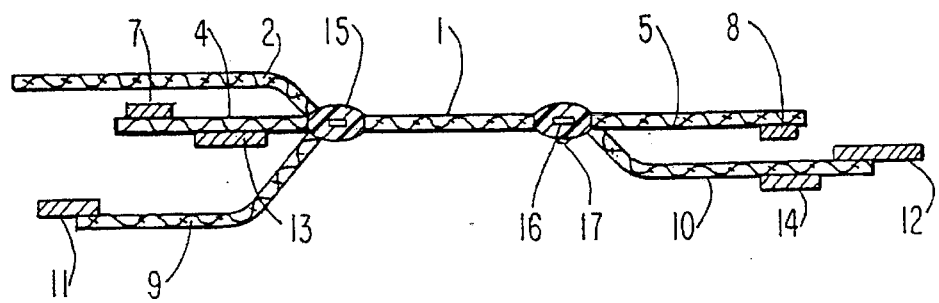
FIG. 2 is a sectional view along line 1—1 of FIG. 1.

Referring to FIG. 1 and FIG. 2, base bandage member 1 is made of pure cotton or elastic fabric. Length T of the base bandage member 1 may be varied to accommodate patients of different size and stature. Width $t_1$ is slightly greater than width $t_2$ when the invention is used as a chest bandage, due to the V-shape, larger on the upper part than on the lower part, of the typical human torso. Width $t_1$ and width $t_2$ of the base bandage member are equal when the invention is used as a general application bandage. Cloth cover 2 is rectangular in shape and made of pure cotton or other sterile fabric. Cloth cover 2 is attached to a edge of base bandage member 1. The length of the cover is equal to length T of base bandage member 1. Horizontal drainage opening 3 is located within cover cloth 2. A drainage tube may pass through drainage opening 3.

Outlying bandage members 4 and 5 are made of elastic fabric. Outlying bandage members 4 and 5 are sewingly attached to base bandage member 1 each on an opposite transverse edge of base bandage member 1. Outlying bandage member 4 is located along the same edge as cloth cover 2. The length of the outlying bandage members is equal to length T. The width of the outlying bandage members is slightly longer than width $t_1$. A drainage opening (not shown) is located on outlying bandage member 4 at a position which corresponds to the drainage opening 3 in cover cloth 2. A drainage opening may optionally be located on outlying bandage member 5 at a position which corresponds to drainage opening 3. Fasteners 7 and 8 may be nylon, plastic, or metallic buttons or other known fastening devices. Fasteners 7 and 8 are respectively attached to distal ends of outlying bandage members 4 and 5. The outlying bandage members can be fastened together by joining fasteners 7 and 8 and the entire bandage can be fixedly bound around a patient.

Safety bandage members 9 and 10 are made of elastic fabric. Safety bandage members 9 and 10 can be used to increase the pressure of the bandage. Safety bandage members 9 and 10 may be attached to base bandage member 1 each on opposite transverse edges of the base bandage member. The length of safety bandage members 9 and 10 is less than length T. The length of safety bandage members 9 and 10 is less than that of outlying bandage members 4 and 5. Fasteners 11 and 12 are respectively attached to distal ends of safety bandage members 9 and 10. Fastener 13 is attached to a central location on a side of outlying bandage member 4, facing safety bandage member 9. Fastener 14 is attached to a central location, corresponding to the location of fastener 13, on a side of safety bandage member 10 opposite outlying bandage member 5. Fasteners 11, 12, 13 and 14 may be nylon, plastic, or metallic buttons or other known fastening devices.

Safety bandage members 9 and 10 are necessary when the present invention is used as a chest bandage or in other applications where added pressure is necessary. When the safety bandage members are used, fasteners 12 and 13 are fastened together, as are fasteners 11 and 14. This increases pressure on the patient's wound.

Padding sheets 15 and 16 are made of foamed plastic or similar materials. Padding sheets 15 and 16 are interposed around the joints formed where outlying bandage members 4 and 5 (or safety bandage members 9 and 10) are attached to base bandage member 1.

Loop 17 is located where outlying bandage member 5 is attached to base bandage member 1, on the same side of the attachment as outlying bandage member 5. Alternately, a loop may also be located where outlying bandage member 6 is attached to base bandage member 1, on the same side of the attachment as outlying bandage member 6. Loop 17 may be used to removably secure receptacles such as bottles or bags on the bandage.

Suspenders 18 and 19 are made of elastic fabric. Suspenders 18 and 19 may be used when the present invention is used as a chest bandage or in other applications whore added support is necessary and available. Suspenders 18 and 19 can be attached to a longitudinal side of base bandage member 1, spaced apart from each other. Connecting strips 20 and 21 can be respectively attached on a longitudinal side, corresponding to the longitudinal side on which the suspenders are attached, of outlying bandage members 4 and 5. Suspender 18 and connecting strip 20, and suspender 19 and connecting strip 21 may be interconnected to each other by either tying them in a knot or by providing fasteners on ends of the connecting strips.

We claim:

1. An elastic bandage for medical use, comprising:
    a. a fabric base bandage member, having two longitudinal and two transverse sides;
    b. two outlying bandage members made of elastic fabric, each having two longitudinal and two transverse sides, each outlying bandage member respectively attached along a transverse side to an opposite transverse side of the base bandage member,
        each outlying bandage member having a distal end opposite its attached transverse side,
        the attached transverse sides of the outlying bandage members each being of a length substantially equal to that of the corresponding transverse sides of the base bandage member,
        at least one outlying bandage member containing a drainage opening;
    c. fasteners located on distal ends of the outlying bandage member.

2. The elastic bandage for metrical use of claim 1, including:
    a. two suspenders, made of elastic fabric, attached to a longitudinal side of the base bandage member, spaced apart from each other; and
    b. two fasteners respectively located on a longitudinal side of each of the outlying bandage members, said longitudinal side of each of the outlying bandage members corresponding to the longitudinal side of the base bandage member on which the suspenders are attached.

3. The elastic bandage for medical use of claim 1, including two thin padding sheets, of length substantially equal to that of the base bandage member, provided in the spaces formed where each of the outlying bandage members is attached to the base bandage member.

4. The elastic bandage for medical use of claim 1, including at least one loop attached to the base bandage member where the outlying bandage members are attached to the base bandage member on a side of the outlying bandage members opposite the cloth cover.

5. An elastic bandage for medical use comprising:

a. a base bandage member, having two longitudinal and two transverse sides, made of fabric;

b. two outlying bandage members, made of elastic fabric, each having two longitudinal and two transverse sides, each outlying bandage member respectively attached along a transverse side to an opposite transverse side of the base bandage member, each outlying bandage member having a distal end opposite its attached transverse side, the attached transverse sides of the outlying bandage member each being of a length substantially equal to that of the corresponding transverse sides of the base bandage member, at least one outlying bandage member containing a drainage opening;

d. two safety bandage members, made of elastic fabric, of length less than that of the base bandage members, attached to the base bandage member where the outlying bandage members are attached to the base bandage member, on a side of the outlying bandage members opposite the cover cloth; and e. fasteners located on distal ends of the safety bandage members, on a side of each safety bandage member facing the base bandage member, at least one fastener located on a surface of one of the outlying bandage members, facing the corresponding safety bandage member, and at least one fastener located on a surface of the other safety bandage member, facing the corresponding outlying bandage member.

6. The elastic bandage for medical use of claim 5, including:

a. two suspenders, made of elastic fabric, attached to a longitudinal side of the base bandage member, spaced apart from each other; and b. two fasteners respectively located on a longitudinal side of each of the outlying bandage members, said longitudinal side of each of the outlying bandage members corresponding to the longitudinal side of the base bandage member on which the suspenders are attached.

7. The elastic bandage for medical use of claim 5, including two thin padding sheets, of length substantially equal to that of the base bandage member, provided in the spaces formed where each of the outlying bandage members is attached to the base bandage member.

* * * * *